United States Patent [19]

Obermann

[11] Patent Number: 4,767,378
[45] Date of Patent: Aug. 30, 1988

[54] FRONTAL MAGNET COUPLING WITH INTEGRATED MAGNETIC BEARING LOAD RELIEF

[75] Inventor: Peter Obermann, Erlangen, Fed. Rep. of Germany

[73] Assignee: Siemens Aktiengesellschaft, Berlin and Munich, Fed. Rep. of Germany

[21] Appl. No.: 891,451

[22] Filed: Jul. 29, 1986

[30] Foreign Application Priority Data

Aug. 1, 1985 [DE] Fed. Rep. of Germany ....... 3527687

[51] Int. Cl.⁴ ...................... H02K 49/10; F16C 39/06; A61M 5/16
[52] U.S. Cl. ...................................................... 464/29
[58] Field of Search ............... 417/420; 464/29; 623/3

[56] References Cited

U.S. PATENT DOCUMENTS

| | | | |
|---|---|---|---|
| 2,241,983 | 5/1941 | Connolly | 464/29 X |
| 2,436,939 | 3/1948 | Schug | 172/284 |
| 2,779,513 | 1/1957 | Dickey | 417/420 X |
| 3,332,252 | 7/1967 | Miller et al. | 417/420 X |
| 3,643,120 | 2/1972 | Young et al. | 464/29 X |
| 4,065,234 | 12/1977 | Yoshiyuki et al. | 464/29 X |
| 4,115,040 | 9/1978 | Knorr | 464/29 X |
| 4,350,646 | 9/1982 | Baus | 417/420 X |

FOREIGN PATENT DOCUMENTS

| | | |
|---|---|---|
| 0034992 | 9/1981 | European Pat. Off. . |
| 1165144 | 3/1964 | Fed. Rep. of Germany . |
| 2049569 | 4/1972 | Fed. Rep. of Germany ...... 417/420 |
| 3338002 | 5/1985 | Fed. Rep. of Germany ...... 417/420 |

Primary Examiner—Daniel P. Stodola
Attorney, Agent, or Firm—Lawrence C. Edelman

[57] ABSTRACT

A frontal magnetic rotational coupling for transmitting torque from a first enclosure to a second enclosure, said enclosures being hermetically separated from each other by an isolating wall. A plate affixed directly above a magnet attached to a rotatable shaft in one enclosure of the coupling is employed to magnetically provide bearing load relief. Axial force exerted upon the magnet from the other enclosure is compensated for by the magnetic field of the magnet itself, due to the return flux path provided by the plate. A miniaturized form of construction results which is of particular advantage when the frontal magnetic rotational coupling is used, for example, in an implantable medication dispensing device.

19 Claims, 1 Drawing Sheet

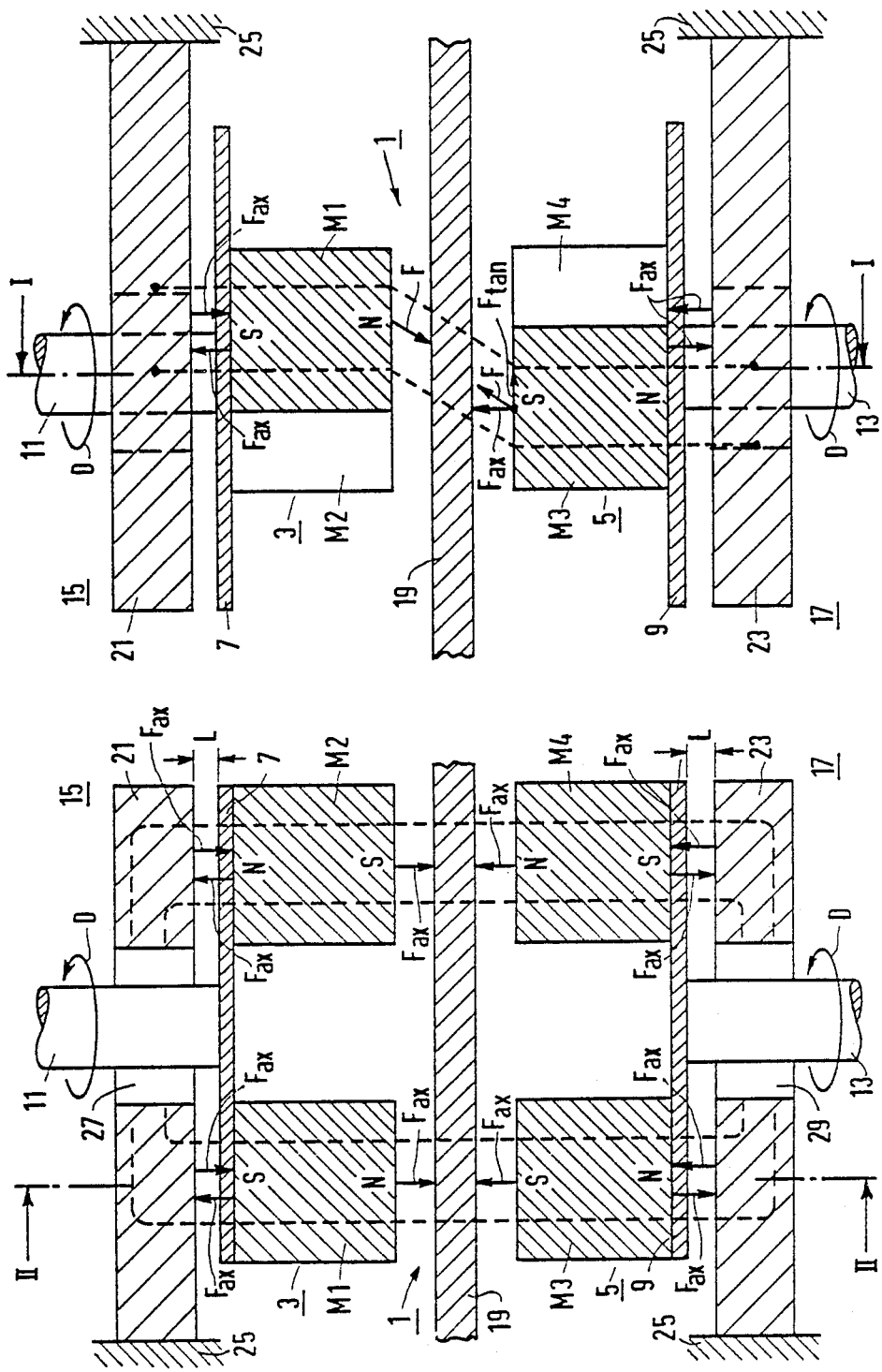

FRONTAL MAGNET COUPLING WITH INTEGRATED MAGNETIC BEARING LOAD RELIEF

BACKGROUND OF THE INVENTION

1. Field of the Invention

The invention relates to a frontal (axial) magnetic coupling provided with at least one magnet for the transfer of torques or forces from a first enclosure to a second enclosure wherein the enclosures are separated by an isolating wall.

2. Description of the Prior Art

A separation of enclosures is necessary when energy (or information) is to be transferred from a first enclosure having specific climatic conditions, into a second enclosure, by mechanical means in response to torques or forces and turning angles or displacements. Climatic conditions prevail in the second enclosure which are different from and incompatible with those present in the first enclosure. Such incompatibility of differing enclosure climatic conditions often arises in procedures involving enclosures of gaseous or liquid media especially if the media are also corrosive, aggressive, poisonous, explosive or radioactive, or if extreme requirements of cleanliness are to apply.

An application involving corrosion may, for example, occur in the case of medication dispensing equipment. Here, extreme requirements relative to dependability and durability are applied. This is of even greater importance in the case of medication dispensing devices which are to be implanted in the body of a patient. Because of the moisture associated with a fluid or gel-like medication, sensitive components, e.g., a motor, electrical contacts or a battery may be functionally impaired or its power output undesirably effected.

In order to remedy this situation, it is useful to divide the medication dispensing device into two regions. This division leads to a dry region in which components to be protected from moisture are located, for example, an electric motor, and a humid region in which those components that come in contact with a liquid medication are located, for example, a pump hose, a medicinal supply reservoir or a pump drive, etc. These two regions are separated from each other by an isolating wall and are hermetically sealed to the outside. The motor and the pump drive are therefore not within the same space, and thus a transmission of forces between the two spaces is necessary. This is made possible by an indirect magnetic coupling which transmits a torque from the first to the second space. One such dispensing arrangement is described in U.S. patent application Ser. No. 658,830 entitled DOSING DEVICE FOR LIQUID, filed in the name of Franetzki, et al., (corresponding to German Publication No. 33 38 002), assigned, like the present application, to Siemens AG and incorporated herein by reference.

It has been shown that because of the attraction due to axial forces of the two parts of a frontal magnetic coupling, a costly bearing construction is necessary in order to insure a definite spacing of the rotating magnets from the dividing wall. Moreover, the force required for the pump drive is often considerably higher, due to friction, than the case where the axial forces are compensated for. Although magnetic means for the relief of bearing loading are known in the technology; they are, however, of limited application in miniaturized equipment, for example in medication dispensing equipment, since they take up substantial space. Such known means for relieving bearing loading are particularly inapplicable to implantable medication dispensing equipment where millimeters must be dealt with in individual components of construction.

SUMMARY OF THE INVENTION

An object of the invention is to develop a frontal magnetic coupling having at least one magnet, in which the axial forces of the attracting magnets are satisfactorily compensated for, while keeping space requirements to a minimum.

This object is achieved, in accordance with the invention, in that in at least one of the enclosures, the frontal magnetic coupling is provided with an arrangement for magnetic bearing load relief, wherein the bearing load relief is derived from the magnetic field of the magnet itself.

By this means, no additional components of construction for supplying the compensating force for bearing load relief need to be integrated. Moreover, the magnetic field available from the magnet of the magnetic coupling is, therefore, not only employed for torque or force transmission, but simultaneously for compensating for the axial force, and thus for bearing load relief. Furthermore, by this means the magnetic coupling rotates more freely since, essentially only the tangential force needs to be supplied for pure torque or force transmission. Compared to conventional magnetic couplings, a magnetic coupling with integrated bearing load relief results in a realtively small and simple form of construction capable of meeting the continuing requirement for miniaturization.

It is advantageous if the frontal magnetic coupling is a rotational frontal magnetic coupling and if bearing load relief is produced by means of a plate of magnetizable material arranged over the free front face of the magnet and separated from it by an air gap. A further and particularly advantageous construction of the invention then results, since the plate is stationary and attached to the drive and/or driven mechanism of the magnetic coupling, and since the frontal face of the drive and/or the driven mechanism is constructed to form the plate. By this means, bearing load relief is achieved without the need for additional space.

Additional advantages and embodiments will follow from the detailed description of the preferred embodiment of the invention and the accompanying figures.

BRIEF DESCRIPTION OF THE INVENTION

FIG. 1 illustrates a section view I—I through a schematic presentation of a frontal magnetic rotational coupling having a respective magnet in each of two compartments; and, FIG. 2 illustrates a section view II—II through the frontal rotational coupling illustrated in FIG. 1.

DESCRIPTION OF THE PREFERRED EMBODIMENT

In the interest of clarity, the frontal magnetic rotational coupling 1 of FIGS. 1 and 2 is presented with its essential elements only. Frontal magnetic rotational coupling 1 comprises a driving element 3 and a driven element 5. The driving and driven elements 3 and 5 are of essentially identical design and are, for example, associated within an implanatable dispensing equipment. Elements 3 and 5 comprise two magnets each M1, M2 and M3, M4, respectively, a magnet support plate 7 and 9, and a shaft 11 and 13, which is firmly attached to magnets M1, M2 and M3, M4 through magnet support plates 7 and 9. Shaft 11 is attached to a driving unit (not shown) which rotates driving element 3 in the direction of the curved arrow D.

Shaft 13 is attached to a driven unit (not shown), which actuates the actual dispensing process. Shaft 13 may, as an example, be connected to the roller carrier of a well known peristaltic pump. Rotation of shaft 13 causes movement of the roller carrier and the medication within the inserted hose is moved to an exit port by the squeezing action imposed by the rollers.

Driving element 3, is located within a first enclosed space 15, which may be referred to as the dry space. In space 15 are located the components and devices which are to be protected from the characteristics of a media which is enclosed in a media space 17. Such components may, for example, be motors, batteries, electrical or mechanical components or meters. Driven element 5 is located within second space 17, which also includes those components which are in contact with the contained medium. Such components, for example, form the actual driven unit. First space 15 is hermetically isolated from second space 17 by an isolating wall 19.

Immediately above magnet support plates 7, 9, and attached to the housing of the dispensing device or another stationary part of the dispensing device, is located a plate 21, 23, respectively, of magnetizable material, e.g. of nickel or soft iron, which serves as a return path for the magnetic flux provided by magnets M1 to M4. The housing or stationary part is indicated by a support block 25. Plates 21, 23 are provided with a clearance hole 27, 29, respectively, at the point at which shafts 11, 13, respectively, must be brought out. Plates 21, 23 exhibit a small air gap L to magnet support plates 7, 9, respectively. Magnet support plates 7, 9 serve exclusively for the mechanical protection of the magnets M1, M2 and M3, M4, respectively, which are imbedded in a casting resin or are otherwise encapsulated. From the point of view of function, or of the magnetic flux of the arrangement, support plates 7, 9 may be eliminated. In that case air gap L is to be inserted directly between plates 21, 23 and magnets M1, M2 and M3, M4. The length of air gap L should have an order of magnitude of one half the spacing of the opposing magnets M1 through M4, which are separated by the isolating wall. In terms of order of magnitude, a percentage difference between the two lengths of up to 50% is acceptable.

The arrangement for providing bearing load relief consists essentially of plates 21, 23, which must be stationary, and of magnets M1 to M4 with their associated air gaps L. As will be seen from the force arrows for the axial (frontal) force Fax, with the proper adjustment of air gap L, no resulting axial force will be operative since the axial force Fax with which the magnets M1, M3 and M2, M4 attract each other, will be compensated for by an opposing second force Fax of equal magnitude, with which the magents M1 through M4, respectively, are drawn to plates 21, 23. This occurs by virtue of their own magnetic field, so that no additional components are needed for bearing load relief. The magnetic flux path (indicated by broken lines in the Figures) is closed through plates 21, 23.

An off-set of the magnets relative to each other, is illustrated in FIG. 2. The diagonally acting force F with which the magnets attract each other may be resolved into a force component Fax, acting in the axial direction of magnets M1 through M4, and a force Ftan, acting in the direction of the indicated frontal magnet rotational coupling. As already described, the force Fax for each of magnets M1 through M4 is compensated, so that only the force Ftan remains. Force Ftan serves for the transmission of the torque. The adjustment of the air gap L between plates 21, 23 and magnets M1, M2 and M3, M4, will depend upon the force F resulting from the desired operating condition of the frontal rotational coupling. The desired operating condition will, from a design point of view, be established by the given values of the transmission parameters, as for example, pump resistance and the desired motor RPM. Once this operating condition and the related air gap is established, no further changes are needed.

A particular advantage of the described frontal rotational coupling for a medication dispensing device is that bearing load relief is provided without additional components of construction, other than plates 21, 23. This is of particular advantage in implantable dispensing devices where space is limited. This space saving effect may be further enhanced if plate 21 is designed to be a part of the driving or motor housing. It can then directly form a frontal surface of the motor housing in which clearance hole 27 serves as a feed through for motor shaft 11. Similarly, it is possible to design second plate 23 as a part of the driven housing or of the pump drive. In both cases it is important that plates 21, 23 are held stationary relative to magnets M1 through M4.

Thus, there has been shown and described novel apparatus for producing a magnetic coupling which fulfills all the objects and advantages sought therefore. Many changes, modifications, variations and other uses and applications of the subject invention will, however, become apparent to those skilled in the art after considering this specification and the accompanying drawings which disclose a preferred embodiment thereof. For example, the application of bearing load relief is not limited to frontal magnetic coupling of the rotational type. In particular, bearing load relief is also applicable to a translationally (longitudinally) operating magnetic displacement coupling. In this case, plate 21 is designed as a lengthwise running part arranged in the longitudinal direction of the intended placement. All such changes, modifications, variations and other uses and applications which do not depart from the spirit and scope of the invention are deemed to be covered by the invention which is limited only by the claims which follow.

What is claimed is:

1. A frontal magnetic coupling provided with at least one magnet for the transmission of torques or forces from a first to a second enclosure of a housing, said enclosures being separated from each other by means of an isolating wall, comprising:
   a driving element coupled for rotation in said first enclosure;
   a driven element coupled for rotation in said second enclosure and axially aligned with said driving element;
   a magnet having a contact surface mechanically coupled to one of said driving and said driven elements;
   an element of magnetizable material coupled to the other one of said driving and said driven elements; and a stationary plate of magnetizable material spaced above the contact surface of said magnet so as to form an air gap therebetween, said plate providing a return path for the magnetic flux of said magnet and thereby providing axial magnetic forces across said air gap which compensates and provides a magnetic bearing load relief of axial magnetic forces between said magnet and said element of magnetizable material.

2. A frontal magnetic coupling according to claim 1, wherein said plate is mechanically coupled to said housing.

3. A frontal magnetic coupling according to claim 2, wherein said housing forms the enclosure for one of said driving and said driven elements that are associated with the magnetic coupling and wherein one surface of the housing is designed to form the plate.

4. A frontal magnetic coupling according to claim 3, wherein:
said plate is provided with a clearance hole for the passage of a drive shaft.

5. A front magnetic coupling according to claim 3, wherein:
said element of magnetizable material is a magnet arranged to axially attract said first mentioned magnet, said first and second mentioned magnets being located in said first and second enclosures, respectively; and
the length of said air gap having an order of magnitude that is one half the distance between said two magnets separated by said isolating wall.

6. A frontal magnetic coupling according to claim 5, wherein:
the length of said air gap may deviate up to 50% from the distance between said magnets separated by the isolating wall.

7. A frontal magnetic coupling according to claim 3, wherein:
said plate is provided with a clearance hole for the passage of a driven shaft.

8. A frontal magnetic coupling according to claim 2, wherein said housing forms a driven enclosure that is associated with the magnetic coupling and wherein a front surface of the driven enclosure forms the plate.

9. A frontal magnetic coupling according to claim 2, wherein said housing forms a driving enclosure that is associated with the magnetic coupling and wherein a front surface of the driving enclosure forms the plate.

10. A frontal magnetic coupling according to claim 2, wherein:
said element of magnetizable material is a magnet arranged to axially attract said first mentioned magnet, said first and second mentioned magnets being located in said first and second enclosures, respectively; and
the length of said air gap having an order of magnitude that is one half the distance between said two magnets separated by said isolating wall.

11. A frontal magnetic coupling according to claim 10, wherein:
the length of said air gap may deviate up to 50% from the distance between said magnets separated by the isolating wall.

12. A frontal magnetic coupling according to claim 11, wherein:
said stationary plate is composed of a soft magnetizable material.

13. A frontal magnetic coupling according to claim 12, wherein:
said magnetizable material is nickel or soft iron.

14. A frontal magnetic coupling according to claim 1 wherein said one of said driving and said driven elements comprises:
a magnet support plate of non-magnetic material
said magnet being affixed to said magnet support plate; and
a shaft affixed to said magnet support plate, said shaft passing through a clearance hole in said stationary plate
and said air gap being provided beteen the magnet support plate and the stationary plate.

15. A frontal magnetic coupling according to claim 14, wherein:
at least two magnets are attached diagonally opposite to each other on said magnet support plate, said two magnets being magnetized with opposing polarities.

16. A frontal magnetic coupling according to claim 15 wherein said isolating wall comprises a portion of a hermetic seal between said first and second enclosures.

17. A frontal magnetic couplng according to claim 1, wherein each of said driving and said driven elements comprise:
a magnet support plate of non-magnetic material, said magnet being affixed to said magnet support plate; and
a shaft affixed to said magnet support plate; and
a stationary plate of magnetizable material spaced above said magnet support plate so as to form an air gap therebetween, said shaft passing through a clearance hole in said stationary plate.

18. A frontal magnetic coupling according to claim 17, wherein:
at least two magnets are attached diagonally opposite to each other on said magnet support plate, said two magnets being magnetized with opposing polarities.

19. A frontal magnetic coupling according to claim 1, wherein:
said element of magnetizable material is a magnet arranged to axially attract said first mentioned magnet, said first and second mentioned magnets being located in said first and second enclosures, respectively; and
the length of said air gap having an order of magnitude that is one half the distance between said two magnets separated by said isolating wall.

* * * * *